US012728126B2

(12) United States Patent
Upadhyay

(10) Patent No.: US 12,728,126 B2
(45) Date of Patent: Sep. 8, 2026

(54) COMPOUNDS FOR INHIBITING LY6K AND METHODS OF USING SAME

(71) Applicant: The Henry M. Jackson Foundation for the Advancement of Military Medicine, Inc., Bethesda, MD (US)

(72) Inventor: Geeta Upadhyay, Washington, DC (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 796 days.

(21) Appl. No.: 17/924,824

(22) PCT Filed: May 14, 2021

(86) PCT No.: PCT/US2021/032497
§ 371 (c)(1),
(2) Date: Nov. 11, 2022

(87) PCT Pub. No.: WO2021/231893
PCT Pub. Date: Nov. 18, 2021

(65) Prior Publication Data

US 2023/0210841 A1 Jul. 6, 2023

Related U.S. Application Data

(60) Provisional application No. 63/025,680, filed on May 15, 2020.

(51) Int. Cl.

| | |
|---|---|
| ***A61K 31/473*** | (2006.01) |
| ***A61K 31/05*** | (2006.01) |
| ***A61P 35/00*** | (2006.01) |

(52) U.S. Cl.
CPC ........... *A61K 31/473* (2013.01); *A61K 31/05* (2013.01); *A61P 35/00* (2018.01)

(58) Field of Classification Search
CPC ........ A61K 31/473; A61K 31/05; A61P 35/00
See application file for complete search history.

(56) References Cited

U.S. PATENT DOCUMENTS

| | | | |
|---|---|---|---|
| 12,134,601 B2 * | 11/2024 | Upadhyay ............ | C07D 219/10 |
| 2006/0111389 A1 | 5/2006 | Neidle et al. | |

FOREIGN PATENT DOCUMENTS

| | | |
|---|---|---|
| WO | WO 2018/006066 A1 | 1/2018 |
| WO | WO 2019/094788 A1 | 5/2019 |

OTHER PUBLICATIONS

Upadhyay, Frontiers in Immunology, Apr. 24, 2019, 10:819 (Year: 2019).*
AlHossiny, Cancer Research; 76(11), 2016 (Year: 2016).*
International Search Report & Written Opinion dated Aug. 13, 2021 for PCT/US2021/032497. 9 pages.
Benti, et al. Small molecule binds with lymphocyte antigen 6K to induce cancer cell death. Cancers. 2020; 12(509):1-12.

* cited by examiner

*Primary Examiner* — Andrew D Kosar
*Assistant Examiner* — Phillip Matthew Rzeczycki
(74) *Attorney, Agent, or Firm* — Sheppard Mullin Richter & Hampton LLP

(57) ABSTRACT

The present disclosure relates to compounds that inhibit Ly6K. Also disclosed are methods of using such compounds to inhibit activity of Ly6K protein in a cell, to inhibit cell proliferation, to modulate expression of a gene in a cell, to reduce suppression of the immune response to cancer in a subject, to decrease tumorigenic growth of a cancer in a subject, and to treat or prevent in a subject a disorder mediated by Ly6K protein.

21 Claims, 3 Drawing Sheets

COMPOUNDS FOR INHIBITING LY6K AND METHODS OF USING SAME

CROSS-REFERENCE TO RELATED APPLICATIONS

This application is a U.S. National Stage Application under 35 U.S.C. § 371 of International Application No. PCT/US2021/032497, filed May 14, 2021, which claims priority to U.S. Provisional Application No. 63/025,680, filed May 15, 2020, each of which is incorporated herein by reference for all purposes.

STATEMENT REGARDING FEDERALLY SPONSORED RESEARCH OR DEVELOPMENT

This disclosure was made with government support under grant numbers R01CA227694 and CA175862 awarded by the National Institutes of Health. The government has certain rights in the invention.

FIELD

The present disclosure relates to compounds and methods of inhibiting Lymphocyte Antigen 6K (Ly6K) protein activity, inhibiting Ly6K positive cancer, and reducing the suppression of immunity against cancer.

BACKGROUND

Triple negative breast cancer (TNBC) is a highly heterogeneous disease and is composed of multiple subtypes. TNBC affects younger women and has the worst overall survival rate among breast cancer subtypes. TNBC patients suffer the worst outcome and have fewer therapeutic options compared to other types of breast cancer patients. Hormone therapies or anti-HER2 therapies do not work for TNBC. Although immunotherapy has led to a paradigm shift in cancer therapeutics, its effect in TNBC has been modest. There is an urgent need to identify and develop novel, effective and safe approaches to treat TNBC.

The increase in expression of immune checkpoint protein PD-L1 in TNBC contributes to tumor immune escape. TGFβ signaling represents another key factor in cancer that activates both immune and non-immune associated pathways of tumor progression. The widespread expression and essential function of TGFβ signaling and PD-L1 in many normal tissues, however, make them problematic targets for therapeutic intervention. Therapeutics and methods that specifically target the TGFβ signaling pathway and PD-L1 expression are urgently needed for cancer therapy, particularly for TNBC.

SUMMARY

Provided herein are compounds and methods for treating diseases characterized by elevated expression of Lymphocyte Antigen 6K (Ly6K) in a subject suffering therefrom.

BRIEF DESCRIPTION OF THE DRAWINGS

The present disclosure can be better understood by reference to the following drawings. The drawings are merely exemplary to illustrate certain features that may be used singularly or in combination with other features and the present disclosure should not be limited to the embodiments shown.

Binding of NSC243928 to LY6K.

DETAILED DESCRIPTION

Figure 1A:
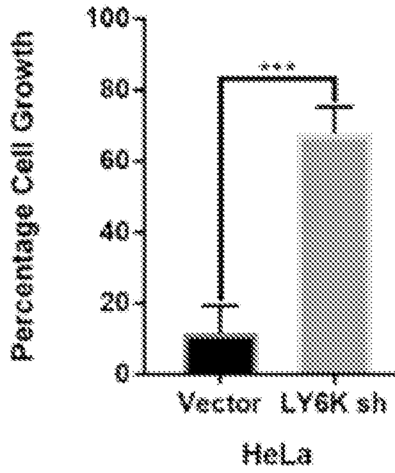
FIG. 1A. HeLa Vector and shRNA2 Cell-Titer-Blue assay. HeLa cells were treated with 2 μM NSC243928. After 24 h, cell viability was assessed (* indicates $P<0.001$).

The following detailed description is presented to enable any person skilled in the art to make and use the subject disclosure. For purposes of explanation, specific nomenclature is set forth to provide a thorough understanding of the present disclosure. However, it will be apparent to one skilled in the art that these specific details are not required to practice the disclosure. Descriptions of specific applications are provided only as representative examples. The present disclosure is not intended to be limited to the embodiments disclosed herein, but is to be accorded the widest possible scope consistent with the principles and features disclosed herein.

This disclosure relates to compounds that inhibit Ly6K and methods of using these compounds.

"Ly6K" refers to lymphocyte antigen 6 family member K proteins. Suitable Ly6K proteins include human Ly6K (e.g., GenBank Accession No. AAI17145.1, which is hereby incorporated by reference in its entirety) and non-human homologs of human Ly6K. Non-human homologs refer to proteins that are structurally and functionally similar to human Ly6K. Homologs have been identified, for example, in other primates (e.g., Pan troglodytes (chimpanzee), *Pongo abelii* (orangutan), *Macaca mulatta* (Rhesus monkey), Gorillas) and in rodents (e.g., mouse, rat).

Inhibition of Ly6K using siRNA technology has been shown to result in decreased levels of ABCC3, ABCG2, FGF-7, NANOG, PSCA, CD34, 2EB1, E-cadherin, and N-cadherin.

E-cadherin is one of the key molecules involved in tumor metastasis. It has been shown that E-cadherin promotes metastasis in diverse models of invasive ductal carcinomas. Loss of E-cadherin reduces cancer cell proliferation and survival, circulating tumor cell number, seeding of cancer cells in distant organs and metastasis outgrowth. E-cadherin is required for metastasis in multiple models of breast cancer.

Homologs of human Ly6K also include, for example, proteins that comprise an amino acid sequence that is at least about 80%, 85%, 90%, 91%, 92%, 93%, 94%, 95%, 96%, 97%, 98%, 99%, or 100% identical to that of human Ly6K. Percent identity as used herein refers to the comparison of one amino acid (or nucleic acid) sequence to another, as scored by matching amino acids (or nucleic acids). Percent identity is determined by comparing a statistically significant number of the amino acids (or nucleic acids) from two sequences and scoring a match when the same two amino acids (or nucleic acids) are present at a position. The percent identity can be calculated by any of a variety of alignment algorithms known and used by persons of ordinary skill in the art.

Compounds

The compounds of the present disclosure include Ly6K inhibitors or a pharmaceutically acceptable salt thereof.

Provided herein is a crystalline form of Compound I. Compound I (also known as N-(4-(acridin-9-ylamino)-3-methoxyphenyl)ethanesulfonamide and NSC243928) has the following structure:

I

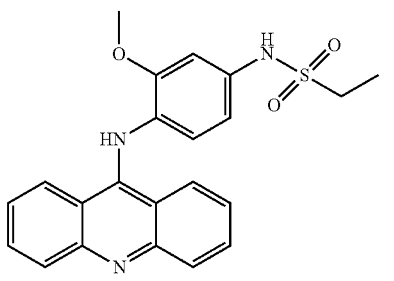

Compound I can be synthesized according to methods known in the art and as described herein.

A crystalline form of Compound I has been characterized via single crystal analysis, and the data is summarized in Table 1.

TABLE 1

Crystal Data for a Crystalline Form of Compound I.

| | |
|---|---|
| Empirical formula | $C_{22}H_{23}N_3O_4S$ |
| Formula weight | 425.49 |
| Temperature/K | 100(2) |
| Crystal system | triclinic |
| Space group | P-1 |
| a/Å | 9.5341(6) |
| b/Å | 11.0364(9) |
| c/Å | 11.0438(9) |
| α/° | 66.285(4) |
| β/° | 82.429(4) |
| γ/° | 66.795(4) |
| Volume/Å$^3$ | 977.36(13) |
| Z | 2 |
| $\rho_{calc}$ g/cm$^3$ | 1.446 |
| μ/mm$^{-1}$ | 0.202 |
| F(000) | 448.0 |
| Crystal size/mm$^3$ | 0.1 × 0.08 × 0.07 |
| Radiation | MoKα (λ = 0.71073) |
| 2Θ range for data collection/° | 4.35 to 52.836 |
| Index ranges | −11 ≤ h ≤ 11, −13 ≤ k ≤ 13, −13 ≤ 1 ≤ 13 |
| Reflections collected | 11172 |
| Independent reflections | 3973 [$R_{int}$ = 0.0495, $R_{sigma}$ = 0.0580] |
| Data/restraints/parameters | 3973/2/309 |
| Goodness-of-fit on F$^2$ | 1.010 |
| Final R indexes [I >= 2σ (I)] | $R_1$ = 0.0486, $wR_2$ = 0.1104 |
| Final R indexes [all data] | $R_1$ = 0.0791, $wR_2$ = 0.1246 |
| Largest diff. peak/hole/e Å$^{-3}$ | 0.43/−0.52 |

In some embodiments, the crystalline form of Compound I is characterized by space group P-1, having the following parameters as collected using MoKα at λ=0.71073: a=9.5341(6) Å; b=11.0364(9) Å; c=11.0438(9) Å; α=66.285(4)°; β=82.429(4)°; and γ=66.795(4)°.

In some embodiments, the volume of a unit cell is 977.36(13) Å.

The compounds of the present disclosure, or pharmaceutically acceptable salts thereof, can optionally be modified to include a tag. A "tag" as used herein includes any labeling moiety that facilitates the detection, quantitation, isolation, and/or purification of a compound (i.e., a compound of the present disclosure, a compound-glutaminase GLS1 protein conjugate as described infra, a conjugated compound/inhibitor as described infra, and/or a conjugated glutaminase GLS1 protein as described infra). Methods for modifying small molecules to include tags are well known in the art. For example, click chemistry (see, e.g., U.S. Pat. No. 7,375,234 to Sharpless et al., which is hereby incorporated by reference in its entirety) may be used to attach a tag to a compound.

Suitable tags include purification tags, labels including radioactive or fluorescent labels, enzymatic tags, prosthetic groups, luminescent materials, bioluminescent materials, positron emitting metals, nonradioactive paramagnetic metal ions, and any other signal suitable for detection and/or measurement by radiometric, colorimetric, fluorometric, size-separation, or precipitation means, or other means known in the art.

Purification tags, such as, but not limited to, maltose-binding protein (MBP–), poly-histidine ($His_{6-}$), or a glutathione-S-transferase (GST–), can assist in compound purification or separation but can later be removed, i.e., cleaved from the compound following recovery. Protease-specific cleavage sites can be used to facilitate the removal of the purification tag. The desired product can be purified further to remove the cleaved purification tags.

Other suitable tags include radioactive labels, such as, $^{125}I$, $^{123}I$, $^{131}I$, $^{111}In$, $^{112}In$, $^{113}In$, $^{115}In$, $^{99}TC$, $^{213}Bi$, $^{14}C$, $^{51}Cr$, $^{153}Gd$, $^{159}Gd$, $^{68}Ga$, $^{67}Ga$, $^{68}Ge$, $^{166}Ho$, $^{140}La$, $^{177}Lu$, $^{54}Mn$, $^{99}Mo$, $^{103}Pd$, $^{32}P$, $^{142}Pr$, $^{149}Pm$, $^{186}Re$, $^{188}Re$, $^{105}Rh$, $^{97}Ru$, $^{153}Sm$, $^{47}Sc$, $^{75}Se$, $^{85}Sr$, $^{35}S$, $^{201}Ti$, $^{113}Sn$, $^{117}Sn$, $^{3}H$, $^{133}Xe$, $^{169}Yb$, $^{175}Yb$, $^{90}Y$, and $^{65}Zn$. Methods of radiolabeling compounds are known in the art and described in U.S. Pat. No. 5,830,431 to Srinivasan et al., which is hereby incorporated by reference in its entirety. Radioactivity is detected and quantified using a scintillation counter or autoradiography. Further examples include positron emitting metals using various positron emission tomographies, and nonradioactive paramagnetic metal ions.

Alternatively, the compound can be conjugated to a fluorescent tag. Suitable fluorescent tags include, without limitation, chelates (europium chelates), fluorescein and its derivatives, rhodamine and its derivatives, dansyl, Lissamine, phycoerythrin, Texas Red, and umbelliferone. The fluorescent labels can be conjugated to the compounds using techniques disclosed in Current Protocols in Immunology (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., Methods for the Preparation of Enzyme—

Antibody Conjugates for Use in Enzyme Immunoassay, in Methods in Enzymology 147-66 (Langone et al. eds., 1981), which is hereby incorporated by reference in its entirety.

Prosthetic group complexes include, but are not limited to, streptavidin/biotin and avidin/biotin. Alternatively, the compound can be conjugated to a luminescent or bioluminescent material including, but not limited to, luminol, luciferase, luciferin, and aequorin.

The compounds of the present disclosure (or pharmaceutically acceptable salts thereof) can optionally be modified to include an attachment to a solid surface, such as a fibrous test strip, a column, a multi-well microliter plate, a test tube, or beads. Methods for attaching small molecules to such surfaces, including covalent attachment (for example via click chemistry, as described supra) as well as non-covalent attachment through the use of antibody-antigen partners, complementary nucleic acids, etc., are well known in the art.

Pharmaceutically acceptable salts include, but are not limited to, amine salts, such as but not limited to, N, N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris (hydroxymethyl) aminomethane; alkali metal salts, such as but not limited to, lithium, potassium, and sodium; alkali earth metal salts, such as but not limited to, barium, calcium, and magnesium; transition metal salts, such as but not limited to, zinc; and other metal salts, such as but not limited to, sodium hydrogen phosphate and disodium phosphate; and also including, but not limited to, salts of mineral acids, such as but not limited to, hydrochlorides and sulfates; and salts of organic acids, such as but not limited to, acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutically acceptable enol ethers include, but are not limited to, derivatives of formula (R)(R)—C═C(R)(OR) where R is hydrogen, alkyl, alkenyl, alkynyl, aryl, heteroaryl, cycloalkyl, or heterocyclyl. Pharmaceutically acceptable enol esters include, but are not limited to, derivatives of formula (R)(R)—C═C(R)(O—C(O)—R) where R is hydrogen, alkyl, alkenyl, alkynyl, aryl, heteroaryl, cycloalkyl, or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

"Alkyl" refers to an unbranched or branched saturated hydrocarbon chain. As used herein, alkyl has 1 to 20 carbon atoms $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. $—(CH_2)_3CH_3$), sec-butyl (i.e. $—CH(CH_3)CH_2CH_3$), isobutyl (i.e. $—CH_2CH(CH_3)_2$) and tert-butyl (i.e. $—C(CH_3)_3$); and "propyl" includes n-propyl (i.e. $—(CH_2)_2CH_3$) and isopropyl (i.e. $—CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

The term "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, and syn-bicyclopropane.

The term "aryl" refers to aromatic monocyclic or polycyclic ring system containing from 6 to 19 carbon atoms, where the ring system may be optionally substituted. Exemplary aryl groups include, but are not limited to, groups such as phenyl, naphthyl, azulenyl, phenanthrenyl, anthracenyl, fluorenyl, pyrenyl, triphenylenyl, chrysenyl, and naphthacenyl. In some embodiments, the aryl is a monocyclic ring system containing from 6 to 9 carbon atoms.

The term "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, or a polycyclic ring system, which may include fused, bridged, or spiro ring systems; and the nitrogen, carbon, or sulfur atoms in the heterocyclyl radical may be optionally oxidized; the nitrogen atom may be optionally quaternized; and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. In some embodiments, the heterocyclyl is a monocyclic ring radical containing from 3 to 9 carbon atoms.

The term "heteroaryl" refers to an aromatic ring radical which consists of carbon atoms and from one to five heteroatoms selected from the group consisting of nitrogen, oxygen, and sulfur. The heteroaryl may be a monocyclic or polycyclic ring system; and the nitrogen, carbon, and sulfur atoms in the heteroaryl ring may be optionally oxidized; the nitrogen may optionally be quaternized. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. In some embodiments, the heteroaryl is a monocyclic or polycyclic ring system containing from 6 to 19 ring atoms. In some embodiments, the heteroaryl is a monocyclic ring system containing from 6 to 9 ring atoms.

Further heterocycles and heteroaryls are described in Comprehensive Heterocyclic Chemistry: The Structure, Reactions, Synthesis and Use of Heterocyclic Compounds Vol. 1-8 (Alan R. Katritzky et al. eds., $1^{st}$ ed. 1984), which is hereby incorporated by reference in its entirety.

Compounds described herein may be administered in the form of a pharmaceutical composition comprising the compound (or a pharmaceutically acceptable thereof) and excipients. The pharmaceutical compositions can comprise a compound of the present disclosure and a pharmaceutically acceptable carrier and, optionally, one or more additional active agent(s) as discussed below.

Numerous standard references are available that describe procedures for preparing various formulations suitable for administering the compounds according to the disclosure. Examples of potential formulations and preparations are contained, for example, in the Handbook of Pharmaceutical Excipients (American Pharmaceutical Association, current edition), Pharmaceutical Dosage Forms: Tablets (Lieberman et al. eds., Marcel Dekker, Inc., pubs., current edition), and Remington's Pharmaceutical Sciences 1553-93 (Arthur Osol ed., current edition), which are hereby incorporated by reference in their entirety.

Any pharmaceutically acceptable liquid carrier suitable for preparing solutions, suspensions, emulsions, syrups and elixirs may be employed in the pharmaceutical composition. Compounds may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, excipients, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

It will be understood that the specific dose level for any particular patient will depend upon a variety of factors, including the activity of the specific compound employed, the age, body weight, general health, sex, diet time of administration, route of administration, rate of excretion, drug combination and the severity of the particular disease undergoing therapy.

Methods of Treatment

The term "inhibit" or "inhibiting" as it applies to inhibiting activity of a Ly6K protein, inhibiting gene expression, inhibiting TGF-β1, SMAD2/3, IFNγ or Stat1 signaling, inhibiting SMAD2/3 or Stat1 phosphorylation, inhibiting PD-L1 expression, or inhibiting PARP means to suppress, decrease, diminish, or lower activity/signaling/phosphorylation/expression. In all cases, inhibition can be partial or complete.

The term "modulating" as it refers to expression of a gene means to increase or decrease expression and includes modulating transcription, translation, and/or post-translational processing. In at least one embodiment, modulating expression means increasing or decreasing the amount of mRNA produced. In at least one embodiment, modulating expression means increasing or decreasing the amount of mature protein produced.

The term "treatment" or "treating" means any manner in which one or more of the symptoms of a disease or disorder are ameliorated or otherwise beneficially altered. Treatment also encompasses any pharmaceutical use of the compositions herein, such as use for treating diseases or disorders mediated by Ly6K. Disorders mediated by Ly6K include disorders in which Ly6K is overexpressed and/or overactive. Suitable disorders include, without limitation, cancer.

As used herein, "therapeutically effective amount" or "therapeutic amount" refers to an amount of a compound as described herein, or a pharmaceutically acceptable salt thereof, that when administered to a patient suffering from a condition, will have the intended therapeutic effect, e.g., alleviation, amelioration, palliation or elimination of one or more manifestations of the condition in the patient. The full therapeutic effect does not necessarily occur by administration of one dose, and can occur only after administration of a series of doses and can be administered in one dose form or multiples thereof. For example, 500 mg of the compound can be administered in a single 500 mg strength tablet or two 250 mg strength tablets. Thus, a therapeutically effective amount may be administered in one or more administrations.

Ly6K is highly expressed in a variety of cancer cells. Ly6K expression has been shown to be significantly increased in at least breast cancer, colorectal cancer, lung adenocarcinoma, lung squamous carcinoma, brain cancer, glioblastoma, glioma, pheochromocytoma, paraganglioma, testicular cancer, thyroid cancer, prostate cancer, adenoid cystic carcinoma, head and neck cancer, esophageal cancer, stomach cancer, thymoma, liver cancer, cholangiocarcinoma, pancreatic cancer, kidney cancer, bladder cancer, mesothelioma, skin cancer, cervical cancer, endometrial cancer, ovarian cancer, hematopoietic cancer, lymphoma, leukemia, bone cancer, sarcomas, uveal melanoma, or melanomas as compared to their normal counterparts. High Ly6K expression has also been shown to be significantly correlated with poor clinical outcome in at least breast cancer, bladder cancer, brain cancer, cancer of the central nervous system, kidney cancer, lung cancer, ovarian cancer, gastric cancer, colorectal cancer, cervical cancer, head and neck cancer, esophageal cancer, and pancreatic cancer.

Ly6K is also more highly expressed in triple negative breast cancer (TNBC), with the mesenchymal, basal, and immunomodulatory subtypes showing the highest expression.

In some embodiments, triple negative breast cancer (TNBC) refers to breast cancer that tests negative for estrogen receptors, progesterone receptors, or large amounts of HER2/neu protein.

Ly6K is highly expressed in human testis tissue but absent in other normal human tissues. Ly6K is also not required for normal cell function except for spermatogenesis. Thus, in some embodiments, the subject is selected from a population in which causing a deleterious effect on male fertility as a result of administering a Ly6K inhibitor would not be a concern, for example in females or in vasectomized and/or sterile males or males without concern of fertility issues.

Some embodiments provide for a method for treating triple-negative breast cancer in a subject in need thereof, comprising administering to the subject a therapeutically effective amount of Compound I, or a pharmaceutically acceptable salt thereof, and a therapeutically effective amount of a PD-L1 inhibitor or a PD-1 inhibitor.

Some embodiments provide for a method for treating an Ly6K-positive cancer or tumor in a subject in need thereof, comprising administering to the subject a therapeutically effective amount of Compound I, or a pharmaceutically acceptable salt thereof, and a therapeutically effective amount of a PD-L1 inhibitor or a PD-1 inhibitor.

In some embodiments, the Ly6K-positive cancer or tumor is breast cancer, colorectal cancer, lung adenocarcinoma, lung squamous carcinoma, brain cancer, glioblastoma, glioma, pheochromocytoma, paraganglioma, testicular cancer, thyroid cancer, prostate cancer, adenoid cystic carcinoma, head and neck cancer, esophageal cancer, stomach cancer, thymoma, liver cancer, cholangiocarcinoma, pancreatic cancer, kidney cancer, bladder cancer, mesothelioma, skin cancer, cervical cancer, endometrial cancer, ovarian cancer, hematopoietic cancer, lymphoma, leukemia, bone cancer, sarcomas, uveal melanoma, or melanoma. In some embodiments, the Ly6K-positive cancer or tumor is a breast cancer or breast tumor. In some embodiments, the breast cancer is a triple-negative breast cancer, mesenchymal breast cancer, basal breast cancer, or immunomodulatory breast cancer. In some embodiments, the Ly6K-positive cancer is a triple-negative breast cancer.

In some embodiments, methods described herein further comprise administration of an anti-cancer therapeutic agent. In some embodiments, methods described herein further comprise administering a therapeutically effective amount of Compound II, or pharmaceutically acceptable salt thereof.

Some embodiments provide for a method for treating Ly6K-positive cancer or tumor in a subject in need thereof, comprising administering to the subject a therapeutically effective amount of Compound I, or a pharmaceutically acceptable salt thereof, and administering a therapeutically effective amount of Compound II, or a pharmaceutically acceptable salt thereof, and a therapeutically effective amount of a PD-L1 inhibitor or a PD-1 inhibitor.

Some embodiments provide for a method of reducing suppression of immune response to cancer in a subject, comprising: administering to the subject an agent under conditions effective to reduce suppression of immune response to cancer in the subject, wherein the agent is Compound I, or a pharmaceutically acceptable salt thereof, and administering a PD-L1 inhibitor or a PD-1 inhibitor.

Some embodiments provide for a method of inhibiting tumorigenic growth of a cancer or tumor in a subject, comprising: administering an agent to the subject under conditions effective to inhibiting tumorigenic growth of a cancer in the subject, wherein the agent is Compound I, or a pharmaceutically acceptable salt thereof, and administering a PD-L1 inhibitor or a PD-1 inhibitor.

In some embodiments, the inhibiting comprises reducing colony formation, invasion, metastasis, or cell migration.

Some embodiments provide for a method of treating, or preventing recurrence of, a disorder mediated by Ly6K protein in a subject in need thereof, the method comprising: administering a therapeutically effective amount of Compound I, or a pharmaceutically acceptable salt thereof, and a therapeutically effective amount of a PD-L1 inhibitor or a PD-1 inhibitor.

In some embodiments, the disorder is mediated by elevated expression of Ly6K protein. In some embodiments, the disorder is a cancer or tumor. In some embodiments, the cancer is breast cancer. In some embodiments, the cancer is triple-negative breast cancer.

Some embodiments provide for a method for treating a triple-negative breast cancer in a subject in need thereof, comprising administering to the subject a therapeutically effective amount of Compound I, or a pharmaceutically acceptable salt thereof, administering a therapeutically effective amount of Compound II, and administering a therapeutically effective amount of a PD-L1 inhibitor or a PD-1 inhibitor.

Some embodiments provide for a method for treating a triple-negative breast cancer in a subject in need thereof, comprising administering to the subject a pharmaceutical composition comprising a therapeutically effective amount of Compound I, or a pharmaceutically acceptable salt thereof, and a therapeutically effective amount of a PD-L1 inhibitor or a PD-1 inhibitor.

Some embodiments provide for a method for treating a triple-negative breast cancer in a subject in need thereof, comprising administering to the subject a pharmaceutical composition comprising a therapeutically effective amount of Compound I, or a pharmaceutically acceptable salt thereof, and a therapeutically effective amount Compound II, or pharmaceutically acceptable salt thereof, and a therapeutically effective amount of a PD-L1 inhibitor or a PD-1 inhibitor.

Some embodiments provide for a method for modulating a tumor microenvironment in a subject in need thereof, comprising reducing myeloid derived suppressor cells by administering to the subject a therapeutically effective amount of Compound I or a pharmaceutically acceptable salt thereof.

Some embodiments provide for a method for modulating a tumor microenvironment in a subject in need thereof, comprising reducing myeloid derived suppressor cells by administering to the subject a therapeutically effective amount of Compound I or a pharmaceutically acceptable salt thereof, and a therapeutically effective amount of a PD-L1 inhibitor or a PD-1 inhibitor.

In some embodiments, the tumor microenvironment is a Ly6K-positive tumor microenvironment.

Some embodiments provide for a method for a disorder mediated by PARP in a subject in need thereof, comprising administering to the subject a therapeutically effective amount of Compound I or a pharmaceutically acceptable salt thereof.

In some embodiments, a disorder mediated by PARP is a cancer. In some embodiments, the cancer is ovarian cancer, breast cancer, bladder cancer, or colon cancer.

Some embodiments provide for a method for treating triple-negative breast cancer in a subject in need thereof, comprising administering to the subject a therapeutically effective amount of a crystalline form of Compound I:

I

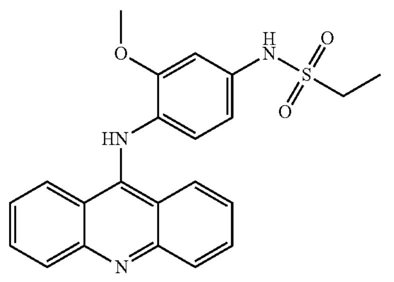

or a pharmaceutically acceptable salt thereof,
wherein the crystalline form is characterized by space group P-1, having the following parameters as collected using MoKα at λ=0.71073:

a=9.5341(6) Å
b=11.0364(9) Å
c=11.0438(9) Å
α=66.285(4)°
β=82.429(4)°
γ=66.795(4)°.

Some embodiments provide for a method for treating an Ly6K-positive cancer or tumor in a subject in need thereof, comprising administering to the subject a therapeutically effective amount of a crystalline form of Compound I, or a pharmaceutically acceptable salt thereof, wherein the crystalline form is characterized by space group P-1, having the following parameters as collected using MoKα at λ=0.71073:

a=9.5341(6) Å
b=11.0364(9) Å
α=66.285(4)°
β=82.429(4)°
γ=66.795(4)°.

In some embodiments, the Ly6K-positive cancer or tumor is breast cancer, colorectal cancer, lung adenocarcinoma, lung squamous carcinoma, brain cancer, glioblastoma, glioma, pheochromocytoma, paraganglioma, testicular cancer, thyroid cancer, prostate cancer, adenoid cystic carcinoma, head and neck cancer, esophageal cancer, stomach cancer, thymoma, liver cancer, cholangiocarcinoma, pancreatic cancer, kidney cancer, bladder cancer, mesothelioma, skin cancer, cervical cancer, endometrial cancer, ovarian cancer, hematopoietic cancer, lymphoma, leukemia, bone cancer, sarcomas, uveal melanoma, or melanoma.

In some embodiments, the Ly6K-positive cancer or tumor is a breast cancer or breast tumor. In some embodiments, the breast cancer is a triple-negative breast cancer, mesenchymal breast cancer, basal breast cancer, or immunomodulatory breast cancer. In some embodiments, the Ly6K-positive cancer is a triple-negative breast cancer.

In some embodiments, the Ly6K-positive cancer is colorectal cancer. In some embodiments, the Ly6K-positive cancer is bladder cancer.

Some embodiments provide for method of inhibiting activity of Ly6K protein in a cell, the method comprising contacting the cell with an agent under conditions effective to inhibit activity of a Ly6K protein in the cell, wherein the agent is Compound I, or a pharmaceutically acceptable salt thereof.

Some embodiments provide for a method of inhibiting activity of Ly6K protein in a cell, the method comprising contacting the cell with an agent under conditions effective to inhibit activity of a Ly6K protein in the cell, wherein the agent is a crystalline form of Compound I, or a pharmaceutically acceptable salt thereof, wherein the crystalline form is characterized by space group P-1, having the following parameters as collected using MoKα at λ=0.71073:

a=9.5341(6) Å
b=11.0364(9) Å
c=11.0438(9) Å
α=66.285(4)°
β=82.429(4)°
γ=66.795(4)°.

Some embodiments provide for a method of inhibiting proliferation of a cell, the method comprising: contacting the cell with an agent under conditions effective to inhibiting proliferation of the cell, wherein the agent is Compound I, or a pharmaceutically acceptable salt thereof.

Some embodiments provide for a method of inhibiting proliferation of a cell, the method comprising: contacting the cell with an agent under conditions effective to inhibiting proliferation of the cell, wherein the agent is a crystalline form of Compound I, or a pharmaceutically acceptable salt thereof, wherein the crystalline form is characterized by space group P-1, having the following parameters as collected using MoKα at λ=0.71073:

a=9.5341(6) Å
b=11.0364(9) Å
c=11.0438(9) Å
α=66.285(4)°
β=82.429(4)°
γ=66.795(4)°.

Some embodiments provide for a method of modulating expression of a gene in a cell, the method comprising: contacting the cell with an agent under conditions effective to modulate the expression of a gene in the cell, wherein the agent is Compound I, or a pharmaceutically acceptable salt thereof, and wherein the gene is selected from the group consisting of PD-L1, ABCC3, ABCG2, FGF-7, NANOG, PSCA, CD34, 2EB1, CDH1 (E-cadherin), and CDH2 (N-cadherin).

Some embodiments provide for a method of modulating expression of a gene in a cell, the method comprising contacting the cell with an agent under conditions effective to modulate the expression of a gene in the cell, wherein the agent is a crystalline form of Compound I, or a pharmaceutically acceptable salt thereof, wherein the crystalline form is characterized by space group P-1, having the following parameters as collected using MoKα at λ=0.71073:

a=9.5341(6) Å
b=11.0364(9) Å
α=66.285(4)°
β=82.429(4)°
γ=66.795(4)°, and wherein the gene is selected from the group consisting of PD-L1, ABCC3, ABCG2, FGF-7, NANOG, PSCA, CD34, 2EB1, CDH1 (E-cadherin), and CDH2 (N-cadherin).

In some embodiments, the cell overexpresses the Ly6K protein.

In some embodiments, the contacting is carried out in vitro, ex vivo, or in vivo.

Some embodiments provide for a method of reducing suppression of immune response to cancer in a subject, comprising administering to the subject an agent under conditions effective to reduce suppression of immune response to cancer in the subject, wherein the agent is a crystalline form of Compound I, or a pharmaceutically acceptable salt thereof, wherein the crystalline form is characterized by space group P-1, having the following parameters as collected using MoKα at λ=0.71073:

a=9.5341(6) Å
b=11.0364(9) Å
c=11.0438(9) Å
$\alpha$=66.285(4)°
$\beta$=82.429(4)°
$\gamma$=66.795(4)°.

Some embodiments provide for a method of inhibiting tumorigenic growth of a cancer or tumor in a subject, comprising administering an agent to the subject under conditions effective to inhibiting tumorigenic growth of a cancer in the subject, wherein the agent is a crystalline form of Compound I, or a pharmaceutically acceptable salt thereof, wherein the crystalline form is characterized by space group P-1, having the following parameters as collected using MoK$\alpha$ at $\lambda$=0.71073:

a=9.5341(6) Å
b=11.0364(9) Å
c=11.0438(9) Å
$\alpha$=66.285(4)°
$\beta$=82.429(4)°
$\gamma$=66.795(4)°.

In some embodiments, the inhibiting comprises reducing colony formation, invasion, metastasis, or cell migration.

Some embodiments provide for a method for treating, or preventing recurrence of, a disorder mediated by Ly6K protein in a subject in need thereof, the method comprising administering a therapeutically effective amount of a crystalline form of Compound I, or a pharmaceutically acceptable salt thereof, wherein the crystalline form is characterized by space group P-1, having the following parameters as collected using MoK$\alpha$ at $\lambda$=0.71073:

a=9.5341(6) Å
b=11.0364(9) Å
c=11.0438(9) Å
$\alpha$=66.285(4)°
$\beta$=82.429(4)°
$\gamma$=66.795(4)°.

In some embodiments, wherein the disorder is mediated by elevated expression of Ly6K protein.

In some embodiments, the disorder is a cancer or tumor. In some embodiments, the cancer is breast cancer. In some embodiments, the cancer is triple-negative breast cancer. In some embodiments, the cancer is colorectal cancer. In some embodiments, the cancer is bladder cancer.

In some embodiments, the methods described herein further comprise contacting the cell with a second agent, wherein the second agent is Compound II:

II

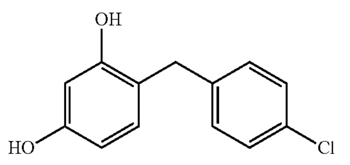

or a pharmaceutically acceptable salt thereof.

Some embodiments provide for a method for treating a triple-negative breast cancer in a subject in need thereof, comprising administering to the subject a pharmaceutical composition comprising a therapeutically effective amount of a crystalline form of Compound I:

I

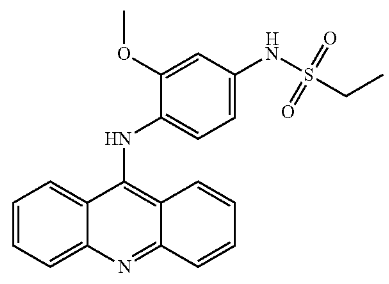

or a pharmaceutically acceptable salt thereof, wherein the crystalline form is characterized by space group P-1, having the following parameters as collected using MoK$\alpha$ at $\lambda$=0.71073:

a=9.5341(6) Å
b=11.0364(9) Å
c=11.0438(9) Å
$\alpha$=66.285(4)°
$\beta$=82.429(4)°
$\gamma$=66.795(4)°.

Some embodiments provide for a method for modulating a tumor microenvironment in a subject in need thereof, comprising reducing myeloid derived suppressor cells by administering to the subject a therapeutically effective amount of a crystalline form of Compound I or a pharmaceutically acceptable salt thereof as described herein. In some embodiments, the tumor microenvironment is a Ly6K-positive tumor microenvironment.

Some embodiments provide for a method for a disorder mediated by PARP in a subject in need thereof, comprising administering to the subject a therapeutically effective amount of a crystalline form of Compound I or a pharmaceutically acceptable salt thereof.

In some embodiments of the present disclosure directed to methods involving contacting a cell with one or more compounds, contacting can be carried out using methods that will be apparent to the skilled artisan, and can be done in vitro, ex vivo, or in vivo.

In some embodiments of the present disclosure, Ly6K-positive tumor cell or cancer cell refers to that the tumor cell or cancer cell has positive expression of Ly6K proteins.

Compounds of the present disclosure may be delivered directly to a targeted cell or tissue or organ. Additionally and/or alternatively, the compounds may be administered to a non-targeted area along with one or more agents that facilitate migration of the compounds to (and/or uptake by) a targeted tissue, organ, or cell. As will be apparent to one of ordinary skill in the art, the compound itself can be modified to facilitate its transport to a target tissue, organ, or cell, including its transport across the blood-brain barrier; and/or to facilitate its uptake by a target cell (e.g., its transport across cell membranes).

In vivo administration can be accomplished either via systemic administration to the subject or via targeted administration to affected tissues, organs, and/or cells, as described above. Typically, the therapeutic agent (i.e., a Ly6K inhibitor compound) will be administered to a patient in a vehicle that delivers the therapeutic agent(s) to the target cell, tissue, or organ. Typically, the therapeutic agent will be administered as a pharmaceutical formulation, such as those described above.

The compounds can be administered, e.g., by intravenous injection, intramuscular injection, subcutaneous injection, intraperitoneal injection, topical application, sublingual, intraarticular (in the joints), intradermal, buccal, ophthalmic (including intraocular), intranasally (including using a cannula), or by other routes. The compounds can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g., WO 97/11682, which is hereby incorporated by reference in its entirety) via a liposomal formulation (see, e.g., European Patent No. 736299, WO 99/59550, and WO 97/13500, which are hereby incorporated by reference in their entirety), via formulations described in WO 03/094886, which is hereby incorporated by reference in its entirety, or in some other form. The compounds can also be administered transdermally (i.e., via reservoir-type or matrix-type patches, microneedles, thermal poration, hypodermic needles, iontophoresis, electroporation, ultrasound or other forms of sonophoresis, jet injection, or a combination of any of the preceding methods (e.g., Prausnitz et al., *Nature Reviews Drug Discovery* 3:115 (2004), which is hereby incorporated by reference in its entirety). The compounds can be administered locally, for example, at the site of injury to an injured blood vessel. The compounds can be coated on a stent. The compounds can be administered using high-velocity transdermal particle injection techniques using the hydrogel particle formulation described in U.S. Patent Publication No. 20020061336, which is hereby incorporated by reference in its entirety. Additional particle formulations are described in WO 00/45792, WO 00/53160, and WO 02/19989, which are hereby incorporated by reference in their entirety. An example of a transdermal formulation containing plaster and the absorption promoter dimethylisosorbide can be found in WO 89/04179, which is hereby incorporated by reference in its entirety. WO 96/11705, which is hereby incorporated by reference in its entirety, provides formulations suitable for transdermal administration.

For use as aerosols, a compound in solution or suspension may be packaged in a pressurized aerosol container together with suitable propellants, for example, hydrocarbon propellants like propane, butane, or isobutane with conventional adjuvants. The compounds also may be administered in a non-pressurized form.

Exemplary delivery devices include, without limitation, nebulizers, atomizers, liposomes (including both active and passive drug delivery techniques) (Wang & Huang, *Proc. Nat'l Acad. Sci. USA* 84:7851-55 (1987); Bangham et al., *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; U.S. Pat. No. 5,059,421 to Loughrey et al.; Wolff et al., Biochim. Biophys. Acta 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the compound to the desired organ, tissue, or cells in vivo.

Contacting (including in vivo administration) can be carried out as frequently as required and for a duration that is suitable to provide the desired effect. For example, contacting can be carried out once or multiple times, and in vivo administration can be carried out with a single sustained-release dosage formulation or with multiple (e.g., daily) doses.

The amount to be administered will, of course, vary depending upon the particular conditions and treatment regimen. The amount or dose required to obtain the desired effect may vary depending on the agent, formulation, cell type, culture conditions (for ex vivo embodiments), the duration for which treatment is desired, and, for in vivo embodiments, the individual to whom the agent is administered.

Effective amounts can be determined empirically by those of skill in the art. For example, this may involve assays in which varying amounts of the compound are administered to cells in culture and the concentration effective for obtaining the desired result is calculated. Determination of effective amounts for in vivo administration may also involve in vitro assays in which varying doses of agent are administered to cells in culture and the concentration of agent effective for achieving the desired result is determined in order to calculate the concentration required in vivo. Effective amounts may also be based on in vivo animal studies.

The compounds can be administered alone or as an active ingredient of a pharmaceutical formulation, such as those described above. The compounds of the present disclosure can be administered in a form where the active ingredient is substantially pure.

A subject or patient in whom administration of the therapeutic compound is an effective therapeutic regimen for a disease or disorder is, in some embodiments, a human, but can be any animal, including a laboratory animal in the context of a clinical trial or screening or activity experiment. Thus, as can be readily appreciated by one of ordinary skill in the art, the methods, compounds and compositions of the present disclosure are particularly suited to administration to any animal, particularly a mammal, and including, but by no means limited to, primates (e.g., humans, chimpanzees, gorillas, orangutans, Rhesus monkeys), domestic animals, such as feline (e.g., cats) or canine (e.g., dogs) subjects, farm animals, such as but not limited to bovine (e.g., cows), equine (e.g., horses), caprine (e.g., goats), ovine (e.g., sheep), and porcine (e.g., pigs) subjects, wild or non-domestic animals (whether in the wild or in a zoological garden), research animals, such as mice, rats, rabbits, guinea pigs, goats, sheep, pigs, dogs, cats, horses, cows, camels, llamas, monkeys, zebrafish, etc., avian species, such as chickens, turkeys, songbirds, etc., i.e., for veterinary medical use.

Combination Therapy

Some embodiments provide for a method of treating a disease or disorder mediated by Ly6K in a subject in need thereof comprising administering to the subject an effective amount of one or more compound(s) as described herein in combination with one or more other therapies or medical procedures effective in treating the disease or disorder. In some embodiments, the disease or disorder is a cancer. In some embodiments, the disease or disorder is Ly6K-positive cancer.

The one or more other therapies or medical procedures include, but are not limited to suitable anticancer therapy (e.g. drug therapy, vaccine therapy, gene therapy, photodynamic therapy, and the like) or medical procedure (e.g. surgery, radiation treatment, hyperthermia heating, bone marrow or stem cell transplant). In some embodiments, the one or more other therapies or medical procedures is selected from: treatment with a chemotherapeutic agent (e.g. chemotherapeutic drug), radiation treatment (e.g. x-ray, gamma.-ray, or electron, proton, neutron, or .alpha. particle beam), hyperthermia heating (e.g. microwave, ultrasound, radiofrequency ablation), vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexatin lutetium), surgery, and bone marrow and stem cell transplantation.

The compounds of the disclosure may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present disclosure, or at the same time as a compound of the disclosure. Use in combination also includes use with a therapy or medical procedure that is administered once or infrequently, such as surgery, along with a compound of the disclosure administered within a short time or longer time before or after the other therapy or procedure. In some embodiments, the present disclosure provides for delivery of compounds of the disclosure and one or more other drug therapeutics delivered by a different route of administration or by the same route of administration. The use in combination for any route of administration includes delivery of compounds of the disclosure and one or more other drug therapeutics delivered by the same route of administration together in any formulation, including formulations where the two compounds are chemically linked in such a way that they maintain their therapeutic activity when administered. In some embodiments, the other drug therapy may be co-administered with one or more compounds of the disclosure. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the disclosure and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

In some embodiments, methods as described herein further comprise administration of an anti-cancer therapeutic agent.

In some embodiments, the anti-cancer therapeutic agent is selected from: an alkylating agent (including but not limited to adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan); an immunotherapy agent selected from a PD-1 and PD-L1 inhibitor; a taxane (including but not limited to DJ-927, docetaxel, TPI 287, paclitaxel and DHA-paclitaxel); an antiangiogenic agent (including but not limited to AE-941 (GW786034, Neovastat), ABT-510, 2-methoxyestradiol, lenalidomide, and thalidomide); a topoisomerase inhibitor (including but not limited to amsacrine, edotecarin, exatecan, irinotecan, SN-38 (7-ethyl-10-hydroxy-camptothecin), rubitecan, topotecan, and 9-aminocamptothecin); and a kinase inhibitor (including but not limited to erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib).

In some embodiments, methods as described herein further comprise administering a therapeutically effective amount of Compound II:

II

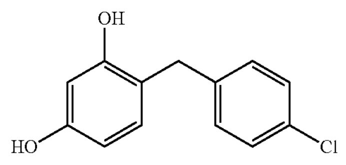

or pharmaceutically acceptable salt thereof.

Compound II, also known as NSC11150 or 4-(4-chlorobenzyl)benzene-1,3-diol, is commercially available.

In some embodiments, an anti-cancer therapeutic agent is a PD-L1 inhibitor. A PD-L1 inhibitor can be an antibody or a small molecule chemical compound. Non-limiting examples of a PD-L1 inhibitor include but are not limited to: atezolizumab (TECENTRIQ®), avelumab (BAVENCIO®), and durvalumab (IMFINZI®). In some embodiments, a PD-L1 inhibitor is BMS-936559 (MDX1105), atezolizumab (TECENTRIQ®), avelumab (BAVENCIO®), or durvalumab (IMFINZI®).

In some embodiments, an anti-cancer therapeutic agent is a PD-1 inhibitor. A PD-1 inhibitor can be an antibody or a small molecule chemical compound. Non-limiting examples of a PD-1 inhibitor include but are not limited to: cemiplimab (LIBTAYO®), nivolumab (OPDIVO®), pembrolizumab (KEYTRUDA®). In some embodiments, PD-1 inhibitor is AMP-224 (2661380), AMP-514 (MEDI0680), CT-011 (pidilizumab), MK-3475 (lambrolizumab), cemiplimab (LIBTAYO®), nivolumab (OPDIVO®), pembrolizumab (KEYTRUDA®), avelumab (BAVENCIO®), durvalumab (IMFINZI®), or atezolizumab (TECENTRIQ®).

In some embodiments, an anti-cancer therapeutic agent is a PARP inhibitor. Non-limiting examples of a PARP inhibitor include but are not limited to olaparib, niraparib, rucaparib, talazoparib AG014699, veliparib, iniparib, MK4827, CEP9722, BMN-673, and E7016.

Some embodiments provide for a method for treating Ly6K-positive cancer or tumor in a subject in need thereof, comprising administering to the subject a therapeutically effective amount of a crystalline form of Compound I, or a pharmaceutically acceptable salt thereof, wherein the crystalline form is characterized by space group P-1, having the following parameters as collected using MoKα at λ=0.71073:

a=9.5341(6) Å
b=11.0364(9) A=
c=11.0438(9) Å
α=66.285(4)°
β=82.429(4)°
γ=66.795(4)°;

and administering a therapeutically effective amount of Compound II, or a pharmaceutically acceptable salt thereof.

Some embodiments provide for a method for treating Ly6K-positive cancer in a subject in need thereof, comprising administering to the subject a therapeutically effective amount of a crystalline form of Compound I, or a pharmaceutically acceptable salt thereof, wherein the crystalline form is characterized by space group P-1, having the following parameters as collected using MoKα at λ=0.71073, a=9.5341(6) Å
b=11.0364(9) A=
c=11.0438(9) Å
α=66.285(4)°
β=82.429(4)°
γ=66.795(4)°, and administering a therapeutically effective amount of Compound II, or a pharmaceutically acceptable salt thereof.

Some embodiments provide for a method for treating a triple-negative breast cancer in a subject in need thereof, comprising administering to the subject a therapeutically effective amount of a crystalline form of Compound I, or a pharmaceutically acceptable salt thereof, wherein the crystalline form is characterized by space group P-1, having the following parameters as collected using MoKα at λ=0.71073:

a=9.5341(6) Å
b=11.0364(9) Å
c=11.0438(9) Å
α=66.285(4)°
β=82.429(4)°
γ=66.795(4)°, and administering a therapeutically effective amount of Compound II, or a pharmaceutically acceptable salt thereof.

Some embodiments provide for a method for treating a triple-negative breast cancer in a subject in need thereof, comprising administering to the subject a pharmaceutical composition comprising a therapeutically effective amount of a crystalline form of Compound I, or a pharmaceutically acceptable salt thereof, wherein the crystalline form is characterized by space group P-1, having the following parameters as collected using MoKα at λ=0.71073:

a=9.5341(6) Å
b=11.0364(9) Å
c=11.0438(9) Å
α=66.285(4)°
β=82.429(4)°
γ=66.795(4)°, and
Compound II, or pharmaceutically acceptable salt thereof.

Some embodiments provide for a method for treating a triple-negative breast cancer in a subject in need thereof, comprising administering to the subject:

a therapeutically effective amount of a crystalline form of Compound I, or a pharmaceutically acceptable salt thereof, and
a PD-L1 inhibitor, wherein the crystalline form is as described herein.

Some embodiments provide for a method for treating a triple-negative breast cancer in a subject in need thereof, comprising administering to the subject:

a therapeutically effective amount of a crystalline form of Compound I, or a pharmaceutically acceptable salt thereof, and
a PD-1 inhibitor, wherein the crystalline form is as described herein.

Some embodiments provide for a method for treating a triple-negative breast cancer in a subject in need thereof, comprising administering to the subject:

a therapeutically effective amount of a crystalline form of Compound I, or a pharmaceutically acceptable salt thereof, and
a PARP inhibitor, wherein the crystalline form is as described herein.

Some embodiments provide for a method for treating a disorder mediated by Ly6K protein in a subject in need thereof, comprising administering to the subject:

a therapeutically effective amount of a crystalline form of Compound I, or a pharmaceutically acceptable salt thereof, and
a PD-L1 inhibitor, wherein the crystalline form is as described herein.

Some embodiments provide for a method for treating a disorder mediated by Ly6K protein in a subject in need thereof, comprising administering to the subject:

a therapeutically effective amount of a crystalline form of Compound I, or a pharmaceutically acceptable salt thereof, and
a PD-1 inhibitor, wherein the crystalline form is as described herein.

Some embodiments provide for a method for treating a disorder mediated by Ly6K protein in a subject in need thereof, comprising administering to the subject:

a therapeutically effective amount of a crystalline form of Compound I, or a pharmaceutically acceptable salt thereof, and
a PARP inhibitor, wherein the crystalline form is as described herein.

Some embodiments provide for a method for treating a triple-negative breast cancer in a subject in need thereof, comprising administering to the subject:

a therapeutically effective amount of a crystalline form of Compound I, or a pharmaceutically acceptable salt thereof, and/or
a therapeutically effective amount of Compound II, and
a PD-L1 inhibitor, wherein the crystalline form is as described herein.

Some embodiments provide for a method for treating a triple-negative breast cancer in a subject in need thereof, comprising administering to the subject:

a therapeutically effective amount of a crystalline form of Compound I, or a pharmaceutically acceptable salt thereof, and/or
a therapeutically effective amount of Compound II, and
a PD-1 inhibitor, wherein the crystalline form is as described herein.

Some embodiments provide for a method for treating a triple-negative breast cancer in a subject in need thereof, comprising administering to the subject:

a therapeutically effective amount of a crystalline form of Compound I, or a pharmaceutically acceptable salt thereof, and/or a therapeutically effective amount of Compound II, and a PARP inhibitor, wherein the crystalline form is as described herein.

Some embodiments provide for a method for treating a disorder mediated by Ly6K protein in a subject in need thereof, comprising administering to the subject:

a therapeutically effective amount of a crystalline form of Compound I, or a pharmaceutically acceptable salt thereof, and/or a therapeutically effective amount of Compound II, and a PD-L1 inhibitor, wherein the crystalline form is as described herein.

Some embodiments provide for a method for treating a disorder mediated by Ly6K protein in a subject in need thereof, comprising administering to the subject:

a therapeutically effective amount of a crystalline form of Compound I, or a pharmaceutically acceptable salt thereof, and/or a therapeutically effective amount of Compound II, and a PD-1 inhibitor, wherein the crystalline form is as described herein.

Some embodiments provide for a method for treating a disorder mediated by Ly6K protein in a subject in need thereof, comprising administering to the subject:

a therapeutically effective amount of a crystalline form of Compound I, or a pharmaceutically acceptable salt thereof, and/or a therapeutically effective amount of Compound II, and a PARP inhibitor, wherein the crystalline form is as described herein.

These aspects of the present disclosure are further illustrated by the following examples. All references cited throughout this application, including in the drawings and Examples, are hereby incorporated by reference in their entirety.

EXAMPLES

The following examples are provided to illustrate embodiments of the present disclosure, but they are by no means intended to limit its scope.

Example 1. Synthesis of Compound I and X-Ray Structure Determination

Synthesis of Compound I was performed according to Scheme 1:

Scheme 1

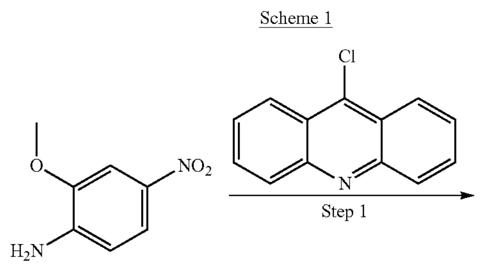

-continued

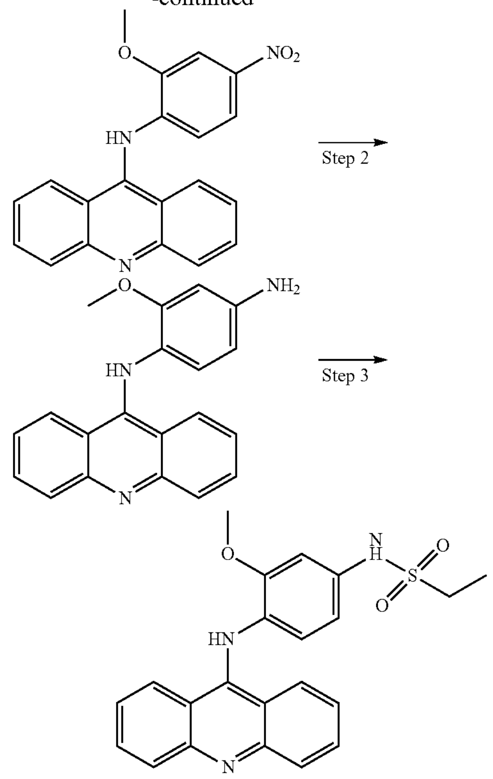

Step 1: Synthesis of N-(2-methoxy-4-nitrophenyl)acridin-9-amine: 2-methoxy-4-nitroaniline (0.842 g, 5.01 mmol) and 9-chloroacridine (0.973 g, 4.55 mmol) were dissolved in N-methyl-2-pyrrolidone (NMP) (17 mL) and two drops of concentrated HCl were added. The reaction was stirred at r.t. for 4 h. Afterwards, ethyl acetate (EtOAc) (about 50 mL) was added to form a precipitate, which was collected by filtration. The solid was redissolved in methanol (MeOH) at 45° C., reprecipitated with EtOAc, and filtered to yield the target product. $^{1}$H NMR (300 MHz, MeOD) δ 8.23 (d, J=8.8 Hz, 2H), 8.07-8.00 (m, 6H), 7.67 (d, J=8.6 Hz, 1H), 7.57-7.52 (m, 2H), 3.69 (s, 3H). $^{13}$C NMR (100 MHz, MeOD) δ 157.46, 154.51, 148.59, 141.49, 137.25, 136.80, 126.69, 126.17, 125.97, 120.45, 118.04, 116.48, 108.79, 56.96.

Step 2: Synthesis of N1-(acridin-9-yl)-2-methoxybenzene-1,4-diamine: 1 (0.800 g, 2.32 mmol) and a catalytic amount of Pd/C were added to 100 mL MeOH in a pressure flask. The resulting suspension was agitated under 50 psi of H2 for 2 h. The suspension was then filtered to remove the Pd/C. The filtrate was evaporated under reduced pressure to yield the crude product, which was carried on without further purification. $^{1}$H NMR (300 MHz, MeOD) δ 8.26 (d, J=8.7 Hz, 2H), 7.94-7.91 (m, 2H), 7.84 (t, J=7.9 Hz, 2H), 7.39 (t, J=7.7 Hz, 2H), 7.16 (d, J=8.3 Hz, 1H), 6.50-6.44 (m, 2H), 3.54 (s, 3H).

Step 3: Synthesis of Compound I: N1-(acridin-9-yl)-2-methoxybenzene-1,4-diamine from step 2 (0.228 g, 0.723 mmol) and dry pyridine (0.086 mL, 1.06 mmol) were added to 3.6 mL of dry dichloromethane (DCM). Ethane sulfonyl chloride (0.206 mL, 2.17 mmol) was then added to the reaction mixture dropwise. Due to toxicity of ethane sulfonyl chloride, the addition was carried out in a fume hood set to an emergency setting with a face velocity around 500 feet per minute and the following PPE was worn: neoprene gloves on top of nitrile gloves, lab coat, face shield. Any materials that came in contact with the reagent were then set in an ice water bath to destroy any residual ethane sulfonyl chloride before being disposed of. The mixture was stirred at room temperature overnight. MeOH was added to destroy any excess ethane sulfonyl chloride and the solvent was evaporated under reduced pressure. The crude mixture was dry loaded on a silica gel column and the product was isolated using the following gradient (100% DCM to 90:10 DCM:MeOH) to yield Compound I. $^1$H NMR (300 MHz, MeOD) δ 8.01 (d, J=8.5 Hz, 2H), 7.67-7.60 (m, 4H), 7.18-7.13 (m, 2H), 6.99 (s, 1H), 6.81 (s, 2H), 3.69 (s, 3H), 3.14 (q, J=7.4 Hz, 2H), 1.35 (t, J=7.4 Hz, 3H). 13C NMR (100 MHz, MeOD) δ 153.53, 152.14, 144.84, 135.59, 135.50, 132.76, 126.75, 123.19, 122.20, 122.03, 119.76, 114.60, 106.61, 56.16, 46.25, 8.48.

X-ray intensity data from an orange wedge-shaped crystal were collected at 100(2) K using a Bruker D8 QUEST diffractometer equipped with a PHOTON-100 CMOS area detector and an Incoatec microfocus source (Mo Kα radiation, λ=0.71073 Å). The raw area detector data frames were reduced and corrected for absorption effects using the Bruker APEX3, SAINT+ and SADABS programs. The structure was solved with SHELXT. Subsequent difference Fourier calculations and full-matrix least-squares refinement against F2 were performed with SHELXL-2018 using OLEX2. The crystal data of a crystalline form of Compound I is summarized in Table 1.

Example 2. Binding of Ly6K

Methods

Surface Plasmon Resonance

Biacore T200 was used for all in vitro surface plasmon resonance (SPR) screening experiments. To test the ability of the small molecules to bind to LY6K-GST, LY6K-GST was covalently immobilized to flow cell 2 (FC2) of a CM5 sensor chip to ≈10,000 RU (response units) using standard amine coupling chemistry in the presence of 10 mM sodium acetate buffer at pH 4.0. A randomly chosen negative control protein (CD99) was also captured on FC4 of the same sensor chip using standard biotin-neutravidin coupling chemistry. HBS-P (10 mM Hepes pH 7.4, 150 mM NaCl, 0.05% v/v surfactant P20) was used as the immobilization/capture running buffer.

FC1 was used as the reference for FC2 and FC3 was used as the reference for FC4. The reference FCs had the same coupling chemistry as the active FCs (FC2 and FC4) but did not have proteins. Small molecules from plates one to nine were injected over these proteins for a period of 60 s at a flow rate of 30 μL/min. After each injection, compounds were allowed to dissociate for 120 s before starting the next compound injection cycle. After every 40 compound injections, multiple blank buffer (PBS-P+5% DMSO or PBS-P+4.75% DMSO+0.25% glycerol) injections were made. Fresh sensor chips and proteins were used for each 384-well plate.

Compound-LY6K and compound-control-protein binding levels were determined after subtracting the non-specific binding to the reference surfaces and response values for the blank buffer injections (double reference subtraction). Theoretical maximum binding levels ($R_{max}$) were calculated, and each molecule's real binding percentage was compared to its corresponding $R_{max}$ value. Compounds binding to the negative control protein more than the target protein were eliminated from further evaluation. Compounds binding to LY6K with 50% or more of the $R_{max}$ were selected as primary hits. Compounds that showed more than 200% $R_{max}$ were considered non-specific aggregates and eliminated from further evaluation. Dose response experiments for LY6D, LY6E, and LY6K were immobilized on FC2, FC3, and FC4 using a standard amine coupling chemistry in the presence of 10 mM sodium acetate buffer at pH values 4.5, 5.5, and 4.0 to levels of ≈800-950 RU, ≈900-1,700 RU, and ≈1,400-3,400 RU, respectively.

Plasmids

N-terminal GST-tagged LY6K was cloned into a mammalian expression vector pEBG with the EF1 promoter. The parent vector was described previously. N-terminal His-tagged mature forms of human LY6K, LY6D, and LY6E were gene synthesized in pET-24a vector (Epoch Biosciences, Bothell, WA, USA).

Mammalian Cell Culture and Transfection

Expression of mammalian LY6K protein in HEK-293T: HEK-293T cells were obtained from ATCC. Cells were cultured in a 37° C. incubator with 5% $CO_2$. Cells were seeded in 100 mm cell culture dishes in DMEM with 10% FBS. Cells were transfected with the pEBG-GST-LY6K plasmid using PolyJet (SignaGen, Rockville, MD, USA) according to manufacturer's protocol. The transfected cells were maintained in culture for 27 h for protein production. After 27 h, the cells were collected, and protein lysates were prepared using RIPA lysis buffer containing 1% glycerol.

LY6K shRNAs and cell lines: LY6K sh1 (Cat #TRCN0000117952), LY6K sh2 (Cat #TRCN0000117953), shRNAs cloned into pLK0.1 were obtained from Sigma Inc. Lentivirus was produced in 293T cells by co-transfection of the pMD2.g and VSVG vectors. At 24 h after transfection, the medium was replaced, and virus was collected. Cells were infected with lentivirus for 24 h in the presence of 4 mg/mL of polybrene, and selection carried out with 1 μg/mL of puromycin. The Hela cells were obtained by Georgetown University core facility. The cell line was authenticated by short random repeat DNA sequencing. Cells were propagated and stored in multiple vials as recommended. Each vial was cells were used and discarded within six months.

Purification of Full-Length GST-LY6K Protein from Mammalian Cells

The cleared protein lysate was subjected to pull down using GST beads (GE Healthcare, Chicago, IL, USA) per manufacturer's instructions. The supernatant was incubated with a 50% slurry of activated Glutathione beads overnight at 4° C. The beads were then centrifuged at 600 g and washed four times with PBS containing 1% Triton X-100, then once with PBS. The proteins were then eluted with an elution buffer containing 40 mM reduced Glutathione (Sigma, St. Louis, MO, USA) solution, 1% Triton X-100, and 1 mM dithiothreitol (DTT). The eluates were analyzed by SDS-PAGE and stained with Coomassie Brilliant Blue. Glutathione was removed from the eluted proteins via buffer exchange with HBS-P buffer (0.01 M HEPES pH 7.4, 0.15 M NaCl, 3 mM EDTA, 0.005% v/v Surfactant P20) using a 3K Amicon Ultra Centrifugal Filter Unit (Millipore, Burlington, MA, USA) for compatibility with Biacore. The eluates were then split into 25 μL aliquots and stored at −80° C. until use.

Purification of Mature Form of LY6K, LY6D, and LY6E Proteins from *E. coli*

Plasmids containing the sequences for N-terminal His-tagged mature LY6 proteins were transformed into BL21 (DE3) *E. coli* via heat shock. The cells were grown, and protein expression was induced with Isopropyl β-D-1-thiogalactopyranoside (IPTG). Following centrifugation, the cell pellet was collected and treated with urea buffer to obtain a protein lysate. A Ni-NTA resin (Roche, Basel, Switzerland) was used in a batch purification method and protein was eluted using imidazole according to the manufacturer's instructions. Protein purity was assessed by SDS-PAGE on a 15% acrylamide gel.

Cell Death Assays

For cell death assay, cells were plated in a black walled 96-well plate and treated with the indicated concentration of drugs for 24 h. Cell-Titer-Blue reagent was added, and the Cytation 5 microplate reader (BioTek, Winooski, VT, USA) was used to measure fluorescence intensity (excitation 560 (10) nm, emission 590(20) nm) according to manufacturer's instructions.

Results

Full-length LY6K was cloned in an N-terminal GST-tagged expression vector and transiently expressed in HEK-293T cells. Protein purification was done using Glutathione Sepharose 4B GST-tagged protein purification resin. Purified recombinant full-length LY6K was immobilized on a CM5 Biacore chip and tested compounds were injected one at a time at a single concentration over the protein-coated surface.

Next, a Cell-Titer-Blue (CTB) functional cell viability assay was performed using tested compounds on LY6K knockdown and control HeLa cells. Stable LY6K shRNA cells were generated by transduction of two different lentiviral shRNA constructs followed by a selection in puromycin. Western blotting confirmed the loss of endogenous LY6K protein in LY6K knockdown cells compared to vector control cells. Vector and LY6K knockdown cell lines were treated with the tested compounds, and the cell viability was determined using a CTB assay. A heat map depicting the percentage of dead cells in green and live cells in red was generated. For this experiment, cell viability was averaged. The average fold change in cell viability (cell viability index) was plotted in LY6K knockdown vs. control cells.

Compounds were also tested for their ability to induce cell death, TGFβ1/Smad2/3 phosphorylation, IFNγ/Stat1 phosphorylation and PD-L1 protein expression.

NSC243928 showed the highest loss in cell death activity in the LY6K knockdown cells. Treatment with NSC243928 in LY6K knockdown shRNA2 cells led to an 8.5-fold decrease in cell death activity compared to vector control HeLa cells (FIG. 1A).

Figure 1B:
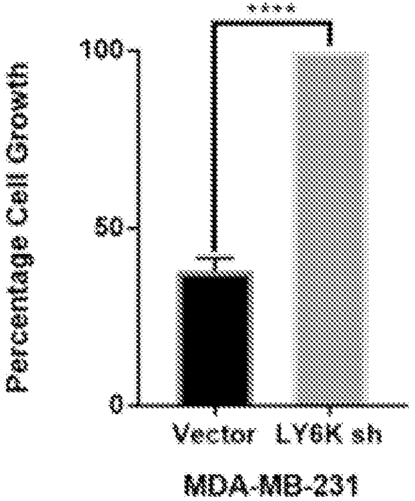
FIG. 1B. MDA-MB-231 Vector and shRNA2 Cell-Titer-Blue assay. MDA-MB-231 cells were treated with 2 μM NSC243928. Cell viability was assessed after 24 h of treatment (** indicates $P<0.0001$).

To confirm the effect of NSC243928 in LY6K-expressing cells, it was observed the parental control and sh2 LY6K knockdown in MDA-MB-231 cells, a triple negative breast cancer cell line. These cells were generated as previously described. To test the effect of NSC243928 on cell growth, the cells were seeded into 96-well plates and treated with 2 μM of the compound for 24 h. A CTB assay was then performed according to manufacturer's instructions to determine the cell growth. It was observed that NSC243928 induces cell death in MDA-MB-231 control cells, while LY6K knockdown cells showed increased cell viability in the presence of NSC243928 (FIG. 1B). These experiments indicate that NSC243928 induces cell death through LY6K pathways.

The $IC_{50}$ of a crystalline form of Compound I and of NSC243928 were studied in cell death assays in HeLa cells.

Example 3. In Vitro Cell Proliferation of Cancer Cells

Figure 2:
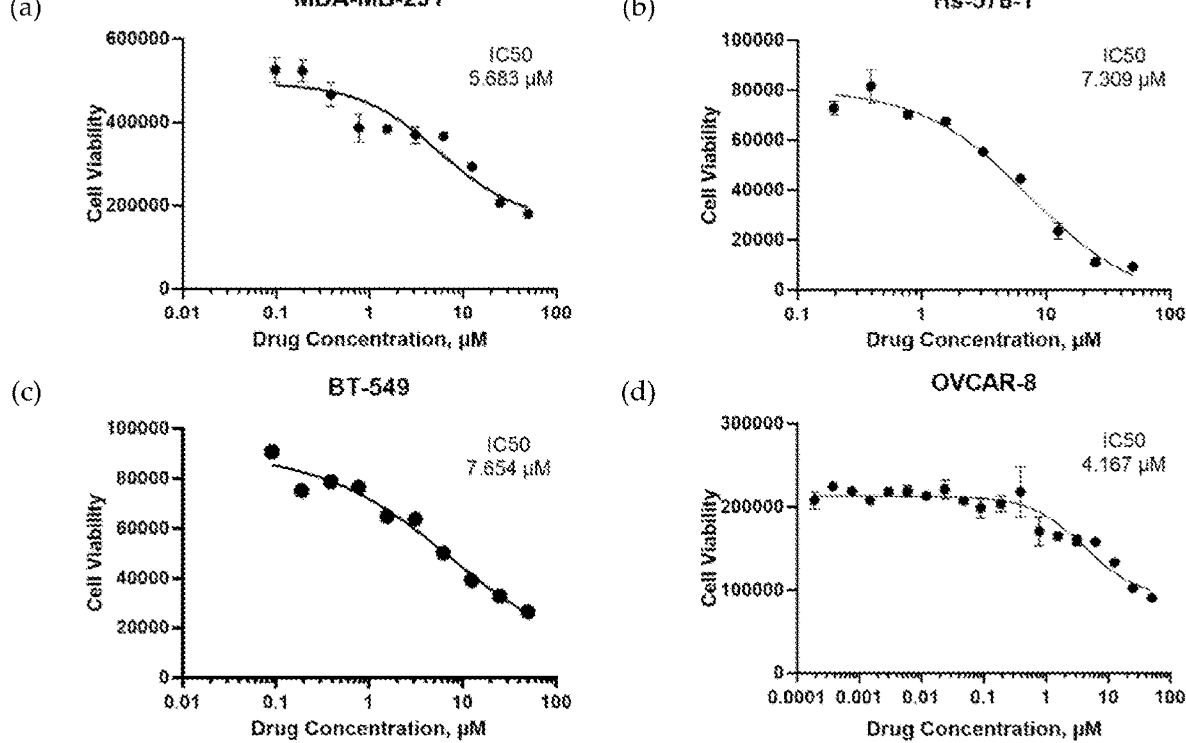
FIG. 2. Cell death activity of a crystalline form of Compound I in cancer cell lines. (A) MDA-MB-231 cells. (B) Hs-578-T cells. (C) BT-549 cells. (D) OVCAR-8 cells.

Cell culture and viability assay are as described herein. 2 μM NSC243928 showed significant inhibitory effect on cell growth of HeLa and MDA-MB-231 cells. However, when Ly6K is knocked down in these cells, the inhibitory effect of NSC243928 is removed (** indicates p<0.0001). The inhibitory effect of a crystalline form of Compound I on cell growth in vitro is further illustrated in other cancer cells types, including Hs-578-T cells, BT-549 cells, and OVCAR-8 cells (FIG. 2**). The $IC_{50}$ of inhibition on cell growth is ranged from 4.167 to 7.654 μM for these cell types. A crystalline form of Compound I showed same or better inhibitory effect on cell growth at different concentrations.

Similarly, NSC11150 also showed inhibitory effect on the proliferation of cells that have high expression levels of PD-L1. Cells were serum starved and treated with 100 ng/ml IFN γ with 2 μM drugs. PD-L1 was measured in live cells (using a zombie live-dead stain). The graph was plotted from three experiments. A 7.9-fold decrease in the number of cells with high PD-L1 expression was observed. It is worthy noting that NSC243928 does not have inhibitory effect on cells with PD-L1 high expression of PD-L1.

Example 4. Inhibition of the Growth of Tumors In Vivo

A syngeneic mammary tumor model is used to show the effect of Ly6K small molecule inhibitors on tumor growth in vivo. 4T1 mouse model is an orthotopic allograft model (also called the spontaneous tumor metastasis model). In the 4T1 mouse model, 4T1 mouse mammary tumor cells were injected into the second mammary gland of syngenetic Balb/c mice, and the spontaneous metastasis to the lung were analyzed with a colonogenic assay. 4T1 mice bearing 50-70 $mm^3$ tumors were treated with NSC243928 or NSC11150 every second day at a dosage of 5 mg/kg in saline. Each group had 10 mice. Tumor measurements were performed using a Vernier caliper. The tumor volumes were calculated using equation ½*length*(width*width).

NSC243928 and NSC11150 have significant inhibitory effects on the tumor growth in vivo. For NSC243928, the inhibition on tumor growth in mice is statistically significant at day 3 following treatment (P<0.005). For NSC11150, the inhibition on tumor growth in mice is statistically significant at day 11 following treatment (P<0.005).

Example 5. Inducing Immunity Against Tumor Recurrence

Treatment of E0771 tumors in a syngeneic C57Bl/6 model with compounds described herein reduced tumor growth, while combination treatment with the two small molecules completely eliminated tumor growth. The treatment was halted after tumor disappearance. Three weeks later, the cured mice were re-challenged with E0771 tumor cells, with complete, durable protection against tumor growth. These results show that compounds described herein have anti-tumor properties and induce host-protective anti-tumor immunity.

In another study, syngeneic female C57BL6 mice were injected with mammary tumor cell line E0771 in the 4th mammary gland. After tumors were palpable, they were injected intra-peritoneal injection every $3^{rd}$ day at 10 mg/kg. The tumor measurements were performed with caliper method. 5 out of 5 control mice continued to sustained tumor growth. 3 out of 5 treated mice showed a complete resolve of mammary tumor. 2 out of 5 treated mice showed partial response. The drug treatment was stopped after the resolve of the tumors. The cured mice (three out of five) were kept under observation for one month. These mice were re-challenged with E0771 tumor cell inoculation into mammary gland. A control naïve group of C57BL6 were simultaneous inoculated with same batch of E0771 tumor cells in to mammary gland. Tumor progression was monitored in both group. Four out of Five naïve mice showed tumor growth. Three out of three cured mice remained immune to tumor cells. Tumor volume was measured in $mm^3$. Thus, Compound I treatment resolves tumor and induces anti-tumor immunity.

Example 6. Ly6K is Required for Increased TGFβ Signaling

Oncomine analysis showed that Ly6K is significantly co-expressed with inflammatory cytokines TGFβ1/2, Bmp2, CXCL10, IFNγ; immunomodulatory proteins PD1, PDL1, CTLA4, CD80, CD25, IDO1 in TNBC vs Non-TNBC. Cells were serum starved overnight and then treated with TGF 13 (10 ng/mL) or IFN γ (100 ng/mL) in the presence of 2 μM NSC243928 or NSC11150 for 30 minutes followed by protein analysis using western blot. NSC243928 diminished the growth of control MDA-MB-231 cells but lost its activity in Ly6K knockdown cells. NSC11150 did not show significant effect on cell death at 2 μM. NSC11150 induced cell death at 100 μM in both control and Ly6K knockdown cells (data not shown). Treatment with NSC11150 led to inhibition of PD-L1 expression in control cells, while NSC243928 did not show significant effect of PD-L1 protein expression. NSC243928 inhibited the TGFβ1 induced phosphorylation of Smad2/3; NSC11150 had no effect on TGFβ1/Smad2/3 signaling. NSC11150 inhibited IFNγ induced phosphorylation of Stat1; NSC243928 had no effect on IFNγ/Stat1 signaling.

Example 7. Inhibition of the Growth of Bladder Cancer Cells

For cell death assay, MB49 cells are plated in a black walled 96-well plate and treated with compounds described herein for 24 h at concentrations of 0.01 μM to 20 μM. Cell-Titer-Blue reagent is added, and the Cytation 5 microplate reader (BioTek, Winooski, VT, USA) is used to measure fluorescence intensity (excitation 560(10) nm, emission 590(20) nm).

To show the inhibition of bladder tumor growth in vivo, MB49 cells are transplanted into C57BL6 mice and grown in vivo. When tumors grow to approximately 50-70 $mm^3$, the mice are treated with Compound I and/or Compound II every second day at a dosage of 5 mg/kg in saline. Each group contains 7-10 mice. Tumor measurements are performed using a Vernier caliper. The tumor volumes are calculated using equation ½*length*(width*width).

Example 8. Inhibition of the Growth of Colorectal Cancer Cells

For cell death assay, colon cancer cell line MC38 cells are plated in a black walled 96-well plate and treated with Compound I and/or Compound II for 24 h at concentrations of 0.01 μM to 20 μM. Cell-Titer-Blue reagent is added, and the Cytation 5 microplate reader (BioTek, Winooski, VT, USA) is used to measure fluorescence intensity (excitation 560(10) nm, emission 590(20) nm).

To show the inhibition of colorectal cancer growth in vivo, MC38 cells are transplanted into C57BL6 mice and grown in vivo. When the tumors grow to approximately 50-70 $mm^3$, the mice are treated with Compound I and/or Compound II every second day at dosage of 5 mg/kg in saline. Each group contains 7-10 mice. Tumor measurements are performed using a Vernier caliper. The tumor volumes are calculated using equation ½*length*(width*width).

Example 9. Combination Therapy

MC38 cells are transplanted into C57BL6 mice and grown in vivo. When the tumors grow to approximately 50-70 $mm^3$ with or without metastatic lesions, the mice are treated with Compound I and/or Compound II every second day at dosage of 5 mg/kg in saline. The mice are also administered a PD-L1 inhibitor or a PD-1 inhibitor. The mice may also be administered a PARP inhibitor. Each group contains 7-10 mice. Tumor measurements are performed using a Vernier caliper. The tumor volumes are calculated using equation ½*length*(width*width).

Example 10. Systemic Anti-Tumor Response

Myeloid-derived suppressor cells (MDSCs) are a major cell type which suppress the anti-tumor response. Cd11b and Gr1 dual positive cells in lymphocytes from peripheral blood from 4T1 tumor bearing mice received Compound I and the control group (10 mice in each group).

Three doses of Compound I (50 mg/kg) was injected via intravenously and intraperitoneally, and intravenous and peripheral blood was collected. Freshly isolated lymphocytes were stained with Cd11b and Gr-1 and a dye which can discriminated live and dead cells. The flow cytometry analysis for dual positivity was performed by gating on the live cells. The Cd11b and Gr-1 dual positive cells were significantly lower in treated group.

Figure 3:
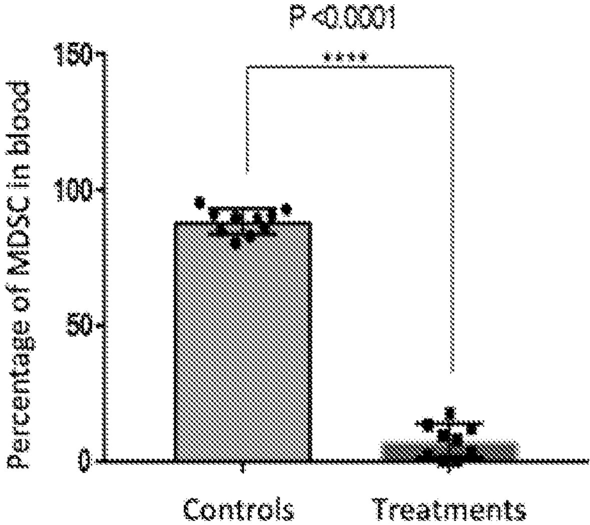
FIG. 3. The graph shows data from 10 mice in each group, showing more than 90% lower myeloid-derived suppressor cells (MDSCs) in peripheral blood of mice which received treatment with Compound I.

Thus, it was found that MDSCs were significantly down-regulated in the treated group. It was also found that Compound I treated mice have less MDSCs in the peripheral blood (more than 90% lower MDSCs in peripheral blood was seen in mice which received treatment)(FIG. 3). This data indicates that treatment with Compound I can activate a systemic anti-tumor immune response.

Example 11. Cellular Morphology Change, Cellular Senescence, and Cell Death

4T1 mammary cancer cells show lack of contact inhibited cell growth, i.e. the cells can grow on top of each other. 4T1 mammary cells were plated at the same cell density. Cells were serum starved overnight. They were supplemented with medium containing 10% serum with or without indicated doses of the Compound I for 16 hours.

Treatment with 0.1 μM and 1.0 μM Compound I inhibited the cellular growth but massive cell death was not observed. At 5.0 μM, reduced cell density was observed, indicating the cell death and/or inhibition of proliferation (Table 2).

TABLE 2

| | % of cells in singlet population | | | | |
|---|---|---|---|---|---|
| | Sub G1 | G1 | S | G2 | 4 n |
| Control | 0.4 | 58.1 | 18.8 | 22.7 | 0.47 |
| 1.0 μM Compound I | 0.59 | 1.84 | 2.27 | 39.8 | 47.3 |
| 5.0 μM Compound I | 7.38 | 67.5 | 2.41 | 0.35 | 0.024 |

It is thus contemplated that treatment with Compound I may lead to suppression of active proliferation, and one of such mechanisms is by induction of cellular senescence. Thus, a beta gal cellular senescence assay was carried out. When treating with very low doses starting from 0.001 to 1.0 μM, there was strong induction of cellular senescence in drug treated cells, and at 5.0 μM, cells density was very low indicating the cell death and/or inhibition of proliferation.

Example 12. DNA Damage Response and Apoptosis

Cancer cells accumulate various mutations in their genome, yet they are protected against DNA damage induced apoptosis. Poly (ADP-ribose) polymerase (PARP) is a protein which facilitates DNA repair, genomic stability, and inhibits programmed cell death. PARP proteins are inactivated by cleavage of caspase 3 and caspase 7 in vivo. PARP inactivation cleavage and caspase activation by western blot was studied.

4T1 mammary cells were plated at the same cell density. Cells were serum starved overnight. They were supplemented with medium containing 10% serum with or without doses of Compound I (0.1 μM, 1.0 μM or 5.0 μM) and for 16 hours. Equal quantity of protein was loaded for western blot analysis.

Cleavage of PARP in a dose dependent manner in parallel to activation of caspase 3 and caspase 7 in a dose dependent manner was observed. PARP inhibition is accompanied by its cleavage by caspase 3 and caspase 7 activation. Caspase activation leads to apoptosis. Caspases are activated by its own cleavage by Apa complexes. Caspase 7 and caspase 3 were activated upon treatment with Compound I. Furthermore, marker of motility RhoA is downregulated in Compound I treated cells. The marker of autophagy LC3B is activated in Compound I treated cells. Total levels of alpha tubulin as loading control were same.

Example 13. Cell Cycle Arrest

4T1 mammary cells were plated at the same cell density. Cells were serum starved overnight. They were supplemented with medium containing 10% serum with or without indicated doses of the Compound I for 16 hours. Cells were washed with PBS to remove floating cells. Cells were collected by trypsinization and centrifugation. Cell were fixed with methanol and counted. Equal number of cells were stained with 5 mM DAPI and flow cytometry was performed on Cytoflex and for flowjo was used for cell cycle analysis.

Compound I treatment leads to cell cycle arrest in G2 phase-2n phase at 1.0 μM Compound I. A closer look at this concentration shows increased accumulation of cells in 4n indicating the cells do not pause for cytokinesis after reaching 2n stage. This suggests that cells will continue to grow in size and eventually die. At 5.0 uM of Compound I, cells were paused in G1 state. At this state, massive apoptosis was observed, and those cells were washed away while collecting cells for cell cycle analysis. Increased subG1 cells was observed in 5.0 μM Compound I, suggesting that even the attached cells were in early apoptosis phase.

Example 13. Short-Term Effect of Compound I Treatment on Localization of Ly6K LY6K is expressed on lamellipodia on the cell membrane. 15 min of treatment with Compound I led to translocation of LY6K from the plasma membrane (0.001 mM Compound I for 15 min). The quantification of percentage of cells positive for LY6K membrane staining showed that even a low dose of Compound I efficiently and promptly removed the LY6K from membrane. This finding is indicating that LY6K translocation is a part of Compound I mechanistic action. It is contemplated that Compound I may disable LY6K signaling by its mislocalization form membrane where LY6K may promote TGFbeta, IFN-gamma signaling paways.

Example 14. Compound I Effect on Overall Levels of Ly6K

4T1 cells were treated with a concentration of 0.1 mM, 1.0 mM, or 5.0 mM of Compound I overnight. Western blotting with LY6K antibody showed a dose response reduction in total level of LY6K.

Thus, treatment with indicated concentration of Compound I reduced total LY6K protein in a dose dependent manner. Loss of LY6K membrane localization was observed at as low as 0.001 mM concentration. Induction of cellular senescence maximum was observed at 0.1 mM. Maximum apoptosis was observed at 5.0 mM concentration. Maximum cell cycle arrest was observed at 1.0 mM concentration. Without being bound to a particular theory, it is contemplated that Compound I affects multiple aspects of cancer cell survival. Compound I may cause loss of LY6K cellular localization, reduce LY6K which can result in cancer cell cycle G2 arrest, cellular senescence, cell death. Taken together, in context of in vivo tumor microenvironment cancer, cell apoptosis can change tumor microenvironment, with increased cancer neoantigen load and trigger the systemic immune response as seen in the in vivo model with loss of MDSCs.

Although certain embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed is:

1. A method for treating triple-negative breast cancer in a subject in need thereof, comprising administering to the subject a therapeutically effective amount of Compound I:

I

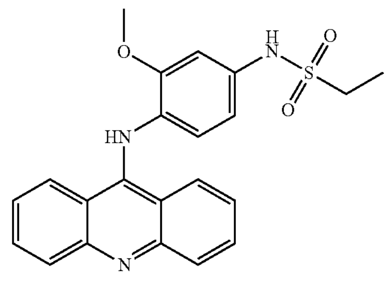

or a pharmaceutically acceptable salt thereof, and a therapeutically effective amount of a PD-L1 inhibitor or a PD-1 inhibitor.

2. A method for treating an Ly6K-positive cancer or tumor in a subject in need thereof, comprising administering to the subject a therapeutically effective amount of Compound I:

I

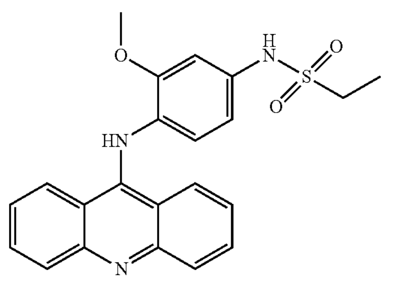

or a pharmaceutically acceptable salt thereof, and a therapeutically effective amount of a PD-L1 inhibitor or a PD-1 inhibitor.

3. The method of claim 2, wherein the Ly6K-positive cancer or tumor is breast cancer, colorectal cancer, lung adenocarcinoma, lung squamous carcinoma, brain cancer, glioblastoma, glioma, pheochromocytoma, paraganglioma, testicular cancer, thyroid cancer, prostate cancer, adenoid cystic carcinoma, head and neck cancer, esophageal cancer, stomach cancer, thymoma, liver cancer, cholangiocarcinoma, pancreatic cancer, kidney cancer, bladder cancer, mesothelioma, skin cancer, cervical cancer, endometrial cancer, ovarian cancer, hematopoietic cancer, lymphoma, leukemia, bone cancer, sarcomas, uveal melanoma, or melanoma.

4. The method of claim 2, wherein the Ly6K-positive cancer or tumor is a breast cancer or breast tumor.

5. The method of claim 4, wherein the breast cancer is a triple-negative breast cancer, mesenchymal breast cancer, basal breast cancer, or immunomodulatory breast cancer.

6. The method of claim 4, wherein the Ly6K-positive cancer is a triple-negative breast cancer.

7. The method of claim 1, further comprising administration of an anti-cancer therapeutic agent.

8. The method of claim 1, further comprising administering a therapeutically effective amount of Compound II:

II

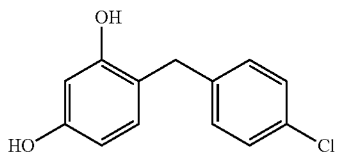

or pharmaceutically acceptable salt thereof.

9. The method of claim 2, further comprising administering a therapeutically effective amount of Compound II:

II

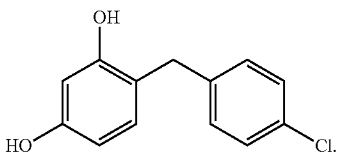

or a pharmaceutically acceptable salt thereof, and a therapeutically effective amount of a PD-L1 inhibitor or a PD-1 inhibitor.

10. A method of reducing suppression of immune response to cancer in a subject, comprising administering to the subject an agent under conditions effective to reduce suppression of immune response to cancer in the subject, wherein the agent is Compound I:

I

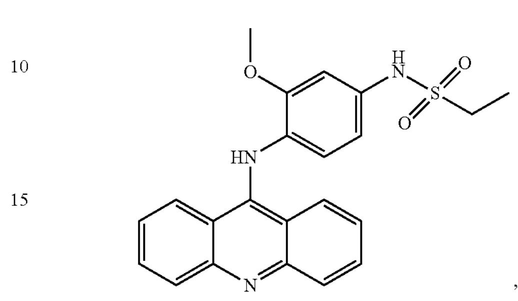

, or a pharmaceutically acceptable salt thereof, and administering a PD-L1 inhibitor or a PD-1 inhibitor.

11. A method of inhibiting tumorigenic growth of a Ly6K-positive cancer or tumor in a subject, comprising administering an agent to the subject under conditions effective to inhibiting tumorigenic growth of a cancer in the subject, wherein the agent is Compound I:

I

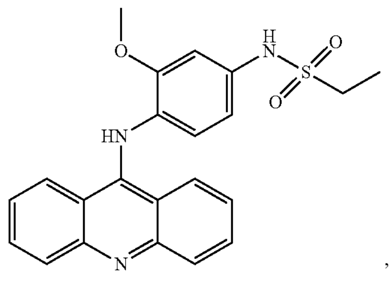

, or a pharmaceutically acceptable salt thereof, and administering a PD-L1 inhibitor or a PD-1 inhibitor.

12. The method of claim 11, wherein the inhibiting comprises reducing colony formation, invasion, metastasis, or cell migration.

13. A method of treating, or preventing recurrence of, a disorder mediated by Ly6K protein in a subject in need thereof, the method comprising:

administering a therapeutically effective amount of Compound I:

I

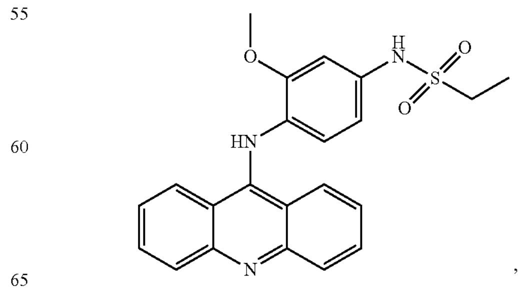

, or a pharmaceutically acceptable salt thereof, and a therapeutically effective amount of a PD-L1 inhibitor or a PD-1 inhibitor.

14. The method of claim 13, wherein the disorder is mediated by elevated expression of Ly6K protein.

15. The method of claim 13, wherein the disorder is a cancer or tumor.

16. The method of claim 15, wherein the cancer is breast cancer.

17. The method of claim 15, wherein the cancer is triple-negative breast cancer.

18. The method of claim 13, further comprising administering to the subject a therapeutically effective amount Compound II:

II

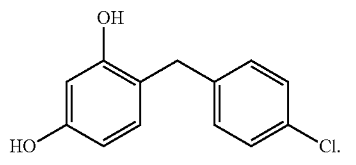

or pharmaceutically acceptable salt thereof.

19. A method for modulating a tumor microenvironment in a subject in need thereof, comprising reducing myeloid-derived suppressor cells by administering to the subject a therapeutically effective amount of Compound I:

I

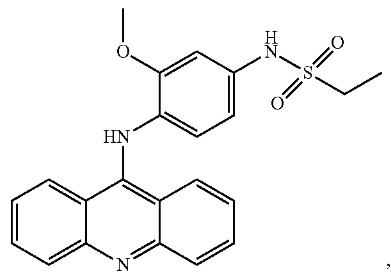

, or a pharmaceutically acceptable salt thereof.

20. The method of claim 19, wherein the tumor microenvironment is a Ly6K-positive tumor microenvironment.

21. The method of claim 19, further comprising administration of an anti-cancer therapeutic agent.

* * * * *